(12) United States Patent
Liu et al.

(10) Patent No.: US 8,421,014 B2
(45) Date of Patent: Apr. 16, 2013

(54) ENERGY DETECTOR AND RELATED APPARATUS

(75) Inventors: James Zhengshe Liu, Glenview, IL (US); Kenneth Scott Kump, Waukesha, WI (US); Habib Vafi, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/156,514

(22) Filed: Jun. 9, 2011

(65) Prior Publication Data

US 2011/0233417 A1 Sep. 29, 2011

Related U.S. Application Data

(62) Division of application No. 11/687,661, filed on Mar. 18, 2007, now Pat. No. 7,973,288.

(51) Int. Cl.
*G01T 1/00* (2006.01)
*H01L 27/146* (2006.01)

(52) U.S. Cl.
USPC .................................. 250/336.1; 250/370.09

(58) Field of Classification Search ............... 250/354.1, 250/395, 370.09; 340/600
See application file for complete search history.

(56) References Cited

U.S. PATENT DOCUMENTS

| | | | |
|---|---|---|---|
| 5,499,281 A | 3/1996 | Weedon et al. | |
| 5,807,254 A | 9/1998 | Meulenbrugge et al. | |
| 6,279,827 B1 | 8/2001 | Yeckley | |
| 6,822,247 B2 | 11/2004 | Sasaki | |
| 7,709,803 B2 * | 5/2010 | Adachi | 250/370.09 |
| 2004/0154815 A1 | 8/2004 | Gustafsson et al. | |

FOREIGN PATENT DOCUMENTS

JP 2002-250772 A 9/2002

* cited by examiner

*Primary Examiner* — David Porta
*Assistant Examiner* — Carolyn Igyarto
(74) *Attorney, Agent, or Firm* — Ziolkowski Patent Solutions Group, SC

(57) ABSTRACT

A portable x-ray detector is disclosed that includes an x-ray detecting member and a user removable electromagnetic interference (EMI) shielding member. The user removable EMI shielding member is positioned to at least partially magnetically shield the x-ray detecting member of the portable x-ray detector by redirecting an impinging magnetic field around the x-ray detecting member. The user removable EMI shielding member includes a first magnetic shielding layer, a second magnetic shielding layer, and an intervening material, other than the x-ray detecting member, between the first magnetic shielding layer and the second magnetic shielding layer.

13 Claims, 5 Drawing Sheets ly illustrating the door or window of the shielding apparatus of FIG. 5.

ENERGY DETECTOR AND RELATED APPARATUS

CROSS-REFERENCE TO RELATED APPLICATION

The present application is a divisional of, and claims priority to, U.S. patent application Ser. No. 11/687,661, filed Mar. 18, 2007, the disclosure of which is incorporated herein.

BACKGROUND OF THE INVENTION

This invention relates generally to imaging methods and apparatus, and more particularly, to portable x-ray detectors and associated apparatus.

Through time, x-ray detectors have been designed to pickup lower and lower energy x-rays. As a result, it also becomes more and more sensitive to interference especially electromagnetic interference (EMI). Portable x-ray detectors are typically moved with the mobile unit all over the hospital and often subjected to varying levels of EMI. This is unlike fixed detectors which are usually housed in special rooms that can be made EMI free or at a very low level.

The EMI can cause image artifacts. Artifact reduction has always been desirable in medical imaging. Therefore, it would be desirable to reduce or eliminate electromagnetic interference.

BRIEF DESCRIPTION OF THE INVENTION

In one aspect, a method includes purposefully electromagnetically shielding a portable x-ray detector.

In another aspect, a method includes detecting for electromagnetic interference on a portable x-ray detector, and prompting a user to perform a purposefully electromagnetically shielding of the portable x-ray detector when electromagnetic interference was detected.

In yet another aspect, a portable x-ray detector is provided. The detector includes an x-ray detecting member, and a user removable electromagnetic interference shielding member positioned to at least partially electromagnetically shield the x-ray detector member.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

Figure 1:
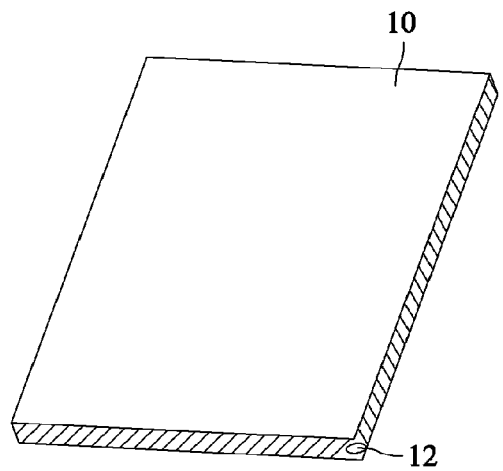
FIG. 1 illustrates a portable x-ray detector.
Figure 2:
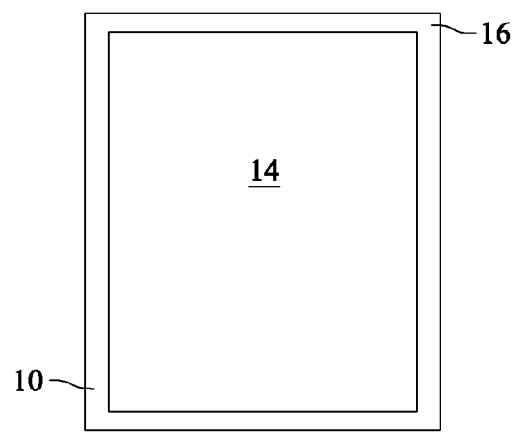
FIG. 2 illustrates that the detector of FIG. 1 includes an x-ray detector member and a user removable electromagnetic interference shielding member positioned to at least partially electromagnetically shield the x-ray detector member.

FIG. 1 illustrates a portable x-ray detector 10 including an opening or port 12 for a cord. FIG. 2 illustrates that detector 10 includes an x-ray detector member 14 and a user removable electromagnetic interference shielding member 16 positioned to at least partially electromagnetically shield the x-ray detector member 14. Although illustrated as a substantially square or rectangular member 16, the function of member 16 is vastly more important than the shape of member 16. In use, member 16 reduces or eliminates any electromagnetic interference that would affect x-ray detector member 14 without shield member 16 being present.

Figure 3:
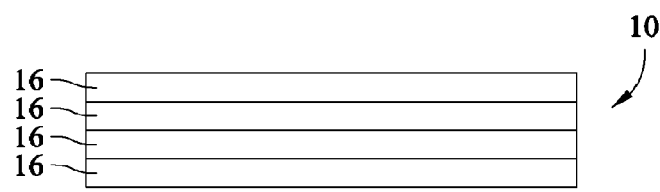
FIG. 3 illustrates a side view of the detector of FIGS. 1 and 2 where a plurality of electromagnetic shields are stacked in layers.

FIG. 3 illustrates a side view of detector 10 where a plurality of electromagnetic shields 16 are stacked in layers. Shields 16 may take different forms. For example, in one embodiment, shields 16 may be a metallic foil with a relatively high permeability. By relatively high permeability, it is meant to be in the range of 1000 henries per meter. In the embodiments of different layers, each layer may be of the same material or different materials may be used depending on the desired electromagnetic energy bands to be covered by the electromagnetic shield(s). For example, aluminum is useful for high frequencies, steel and Amunickle are useful for medium frequencies, and Amumetal is useful for low frequencies. Amunickle and Amumetal are both commercially available from the Amuneal Manufacturing Corp of Philadelphia, Pa. Of course, these are examples set forth for illustration purposes and not for limitation purposes, and there are many suitable materials useful as electromagnetic shielding materials. By low frequencies it is meant the range of less than about 100 kilohertz, medium frequencies mean about 100 kilohertz to about 800 kilohertz, and high frequencies mean above about 800 kilohertz.

Figure 4:
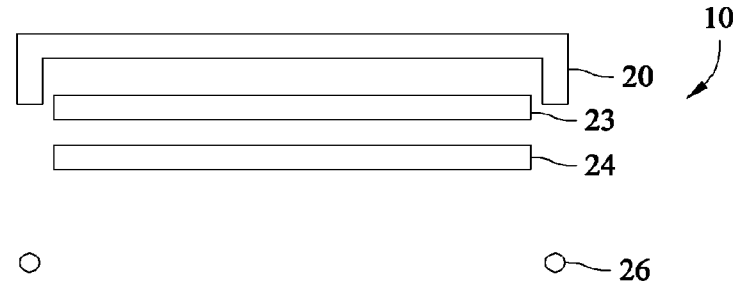
FIG. 4 illustrates the detector of FIGS. 1-3 with a top cover piece, and a bottom cover piece.
Figure 4:

FIG. 4 illustrates an exploded view of detector 10 with a top cover piece 20, a bottom cover piece 22, a carbon graphite piece 23, and an electromagnetic shield 24 positioned beneath the carbon piece 23 and sized to overlap into the area where the top 20 and the bottom 22 meet at the sides. In one embodiment, a gasket 26 is also positioned in the area where the top 20 and the bottom 22 meet at the sides. The gasket is, in one embodiment, made of material selected for its electromagnetic shielding properties such that the gasket acts to reduce or eliminate electromagnetic interference in detector 10. Although illustrated with a separate shield 24, in one embodiment, one or both of top 20 and bottom 22 are fabricated from material selected for its electromagnetic shielding properties such that the top 20 and/or the bottom 22 act to reduce or eliminate electromagnetic interference in detector 10. The fabrication may be such that layers of different material are used to achieve the desired shielding, or a compound with the desired electromagnetic characteristic(s) is used to mold or otherwise create either or both of top 20 and bottom 22. The use of material with the desired EMI deadening characteristics along with other material with the desired structural properties in a compound allows for a unified detector support structure that provides both support and EMI shielding in a single package.

Figure 5:
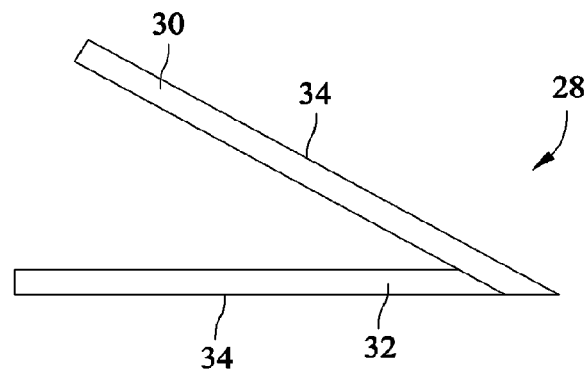
FIG. 5 illustrates an electromagnetic shielding apparatus including a top portion and a bottom portion.
Figure 6:
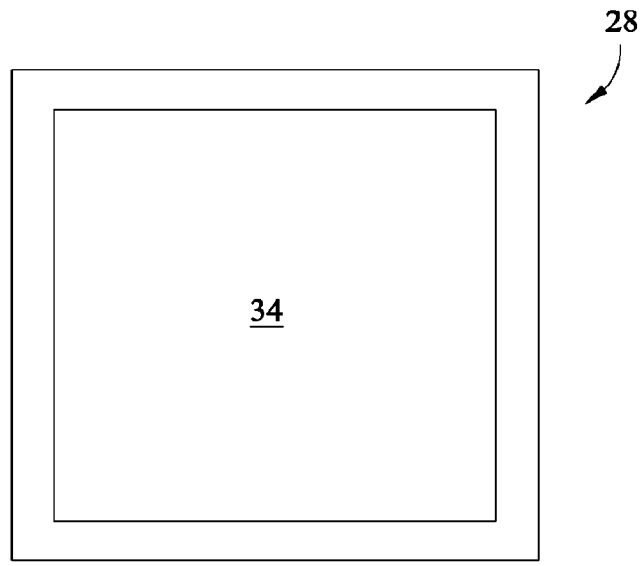
FIG. 6 is a top view, better illustrating the door or window of the shielding apparatus of FIG. 5.

FIG. 5 illustrates an electromagnetic shielding apparatus 28 including a top portion 30 and a bottom portion 32. One or both of the top and the bottom portions 30 and 32 include a window or door 34, in which electromagnetic shielding structure may be placed and removed. FIG. 6 is a top view, better illustrating the door or window 34. Referring back to FIG. 5, apparatus 28 is sized to receive and enclose an x-ray detector such as detector 10. Apparatus 28 allows for the electromagnetic shielding of a detector which was not manufactured with purposeful electromagnetic shielding. In other words, apparatus 28 facilitates adding purposeful electromagnetic shielding to a detector without purposeful electromagnetic shielding in a retrofit manner.

Figure 7:
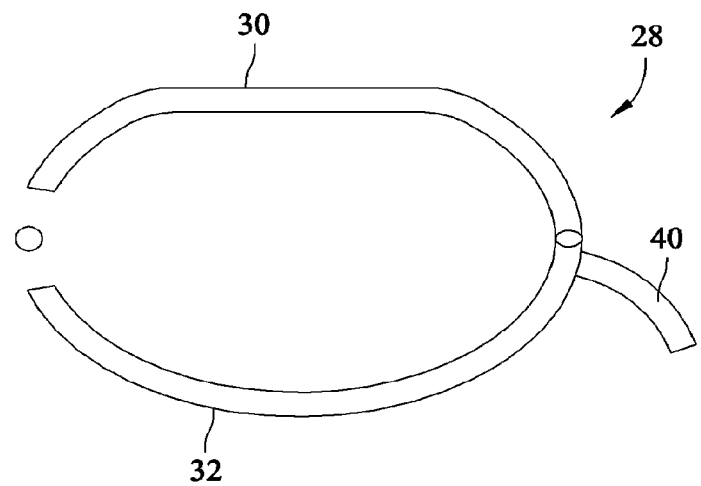
FIG. 7 illustrates shielding apparatus having a clamshell shape.
Figure 8:
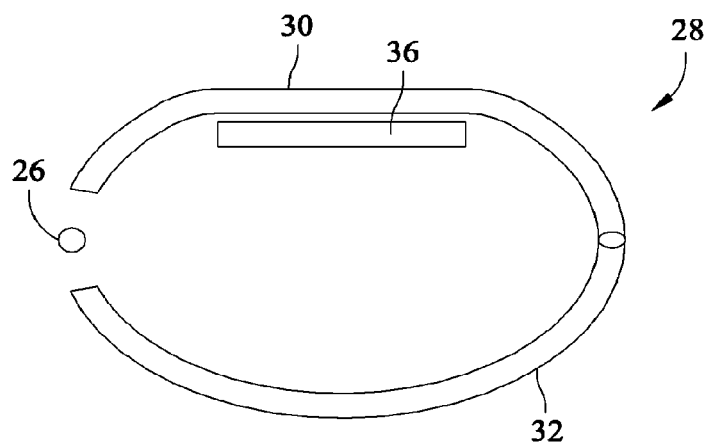
FIG. 8 illustrates that a separate shield is also envisioned.

FIG. 7 illustrates apparatus 28 having a clamshell shape. FIG. 7 further illustrates a gasket 26 where top half 30 and bottom half 32 meet. Also illustrated is a cord 40 that may be a power cord or a data cord, and in one embodiment is also electronically shielded. Additionally, it might be desirable to provide additional EMI shielding to components of the detector instead of all of the detector, and as used herein the phrase "shielding a portable x-ray detector" means at least partially shielding, and is not to be limited to totally shielding only. In FIG. 7 it is illustrated that apparatus 28 is constructed such that it itself acts as an electromagnetic shield. However, and as illustrated in FIG. 8, a separate shield 36 is also envisioned. Although illustrated as one shield 36, other embodiments use multiple shields. And it has been empirically determined that stacking two low x-ray attenuating films as two layers is better than using a single layer of thickness equal to the two layers. In other words, using two 0.25 mm films with stuffing material in between is more effective at reducing or eliminating electromagnetic interference than using one 0.5 mm film.

Figure 9:
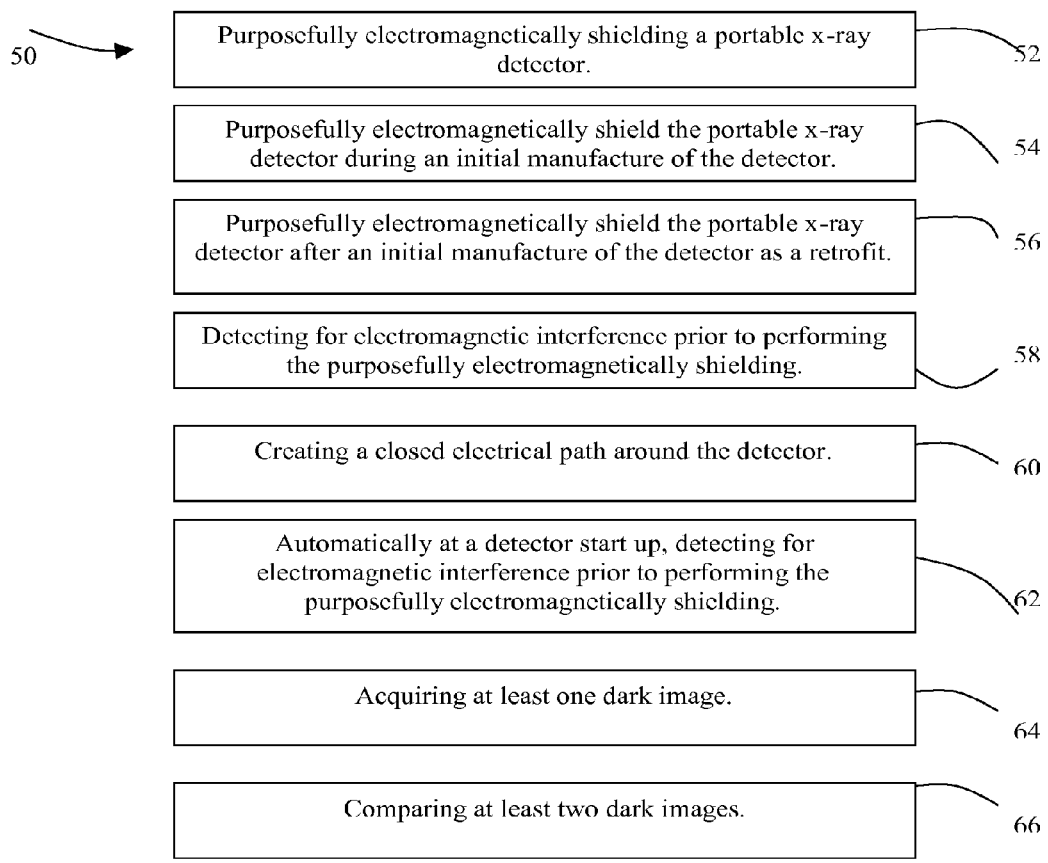
FIG. 9 illustrates a method including the step of purposefully electromagnetically shielding a portable x-ray detector.

FIG. 9 illustrates a method including the step of purposefully electromagnetically shielding 52 a portable x-ray detector. It should be noted that heretofore x-ray detectors included a plurality of parts and circuits such as scintillators, photodiodes, capacitors, etc. and there may have been some incidental electromagnetic shielding inherent to the positioning of the different parts and/or the housing that the parts fit inside. However, it is believed, that no purposefully electromagnetically shielding was done heretofore for a portable x-ray detector.

One option is to purposefully electromagnetically shield 54 the portable x-ray detector during an initial manufacture of the detector. Another option is to purposefully electromagnetically shield 56 the portable x-ray detector after an initial manufacture of the detector as a retrofit. In other words, an existing portable x-ray detector, manufactured without any purposeful electromagnetic shielding may be retrofitted with an electromagnetic shield using the herein described methods and apparatus. In one embodiment, prior to performing the purposefully electromagnetically shielding step 52, electromagnetic interference is detected 58. In one embodiment, the electromagnetic shield is created by creating 60 a closed magnetic path around the detector. Additionally, detecting for electromagnetic interference may be done automatically as part of a detector start up sequence. In other words, when the detector is first turned on, among other typical start up activities like loading detector cell correction vectors or values, part of the sequence includes detecting for EMI (electromagnetic interference).

There are different ways to detect for EMI. One way found useful is to acquire 64 at least one dark image. As used herein the term dark image refers to images obtained with the x-ray source turned off. In the embodiments including detecting EMI, it is anticipated that a user can scan without the EMI shield present when no EMI is present. This is useful because any EMI shield inherently absorbs at least some x-rays. Therefore, there is a trade off between patient x-ray dosing and EMI shielding, and in many embodiments, the user is notified that no substantial EMI is present. As in any physical real world situation, EMI is always present. Therefore, a predetermined limit on EMI is used. In one embodiment, different limits are used for different frequency. Additionally, the EMI can not actually be stopped per se, but the EMI can be re-directed. For example, one embodiment creates a closed magnetic path around the director that re-directs the magnetic field such that the detector is EMI reduced to below the desired level. One technical effect of the herein described methods and apparatus is the reduction of EMI.

The dark image may be acquired when performing what is called a detector scrubbing. A detector scrubbing is when the capacitors are fully charged and the detector is then polled. As is known in the art, the detector has a scintillator layer that receives x-rays, and converts the x-rays to visible light. The visible light then impinges a photodiode that is connected to capacitors in image acquisition mode. However, in detector scrubbing mode, the capacitors are kept artificially at full charge. By artificially it is meant other than from the photodiodes receiving converted photons. Additionally, in some embodiment two dark images are obtained and compared to detect the presence or level of EMI present. For example, one dark image can be generated in a known EMI free location and this image is saved. Then during each power up (at any location) a second dark image is generated, and by comparing the two images it can be determined if EMI is present and at what levels.

It is contemplated that the benefits of the invention accrue to non-human imaging systems such as those systems typically employed in small animal research. In addition, it is contemplated that the benefits of the invention accrue to non-medical imaging systems such as those systems typically employed in an industrial setting or a transportation setting, such as, for example, but not limited to, a baggage scanning CT system for an airport or other transportation center.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A portable x-ray detector comprising:
   an x-ray detecting member; and
   a user removable electromagnetic interference (EMI) shielding member positioned to at least partially magnetically shield the x-ray detecting member of the portable x-ray detector by redirecting an impinging magnetic field around the x-ray detecting member, wherein the user removable EMI shielding member comprises:
      a first magnetic shielding layer;
      a second magnetic shielding layer;
      an intervening material, other than the x-ray detecting member, between the first magnetic shielding layer and the second magnetic shielding layer and
      a carbon graphite piece positioned between the first magnetic shielding layer and the intervening material, the carbon graphite piece configured to provide support to the EMI shielding member.

2. A detector in accordance with claim 1 wherein the EMI shielding member comprises a clam shell.

3. A detector in accordance with claim 2 further comprising an EMI resistant gasket positioned between a top of the shell and a bottom of the shell.

4. A detector in accordance with claim 1 wherein the EMI shielding member comprises a relatively high permeability foil.

5. A detector in accordance with claim 1 wherein the first magnetic shielding layer, the intervening material, and the second magnetic shielding layer are stacked such that the first magnetic shielding layer is adjacent to the intervening material and the second magnetic shielding layer is also adjacent to the intervening material.

6. A detector in accordance with claim 1 wherein the EMI shielding member is configured to form a closed magnetic path around the x-ray detecting member to redirect the impinging magnetic field around the x-ray detecting member.

7. An x-ray detector comprising:
- an x-ray detecting member; and
- a user removable electromagnetic interference (EMI) shielding device selectively positioned about the x-ray detecting member to at least partially magnetically shield the x-ray detecting member;
- wherein the EMI shielding device is configured to form a closed magnetic path around the x-ray detecting member to redirect the impinging magnetic field around the x-ray detecting member so as to provide magnetic shielding; and
- wherein the EMI shielding device comprises:
  - a top cover piece;
  - a bottom cover piece;
  - an intervening material, other than the x-ray detecting member, positioned between the top and bottom cover pieces and configured to provide electromagnetic shielding; and
  - a carbon graphite piece positioned between the top cover piece and the intervening material, the carbon graphite piece configured to provide support to the EMI shielding device;
  - wherein the top and bottom cover pieces are configured such that the top and bottom cover pieces meet along side surfaces thereof.

8. The detector of claim 7 wherein the top and bottom cover pieces are composed of material configured to provide electromagnetic shielding.

9. The detector of claim 7 further comprising an EMI resistant gasket positioned between the top and bottom cover pieces at a location where the side surfaces thereof meet.

10. The detector of claim 7 wherein the top and bottom cover pieces comprise clamshell-shaped pieces.

11. The detector of claim 7 wherein the EMI shielding device is formed, at least in part, of a electromagnetic shielding foil having a permeability of approximately 1000 henries per meter.

12. The detector of claim 7 wherein the user removable EMI shielding device is configured as a retrofittable shielding device that is addable to an existing x-ray detecting member.

13. A retrofit kit comprising:
- a user removable electromagnetic interference (EMI) shielding member configured to be positionable relative to an x-ray detecting member to at least partially magnetically shield the x-ray detecting member by redirecting an impinging magnetic field around the x-ray detecting member, the user removable EMI shielding member comprising:
  - a first magnetic shielding layer;
  - a second magnetic shielding layer;
  - an intervening material, other than the x-ray detecting member, between the first magnetic shielding layer and the second magnetic shielding layer; and
  - a carbon graphite piece positioned between the first magnetic shielding layer and the intervening material, the carbon graphite piece configured to provide support to the EMI shielding member.

* * * * *